US009341835B2

(12) United States Patent
Gu et al.

(10) Patent No.: US 9,341,835 B2
(45) Date of Patent: May 17, 2016

(54) VIRTUAL TELEMICROSCOPE

(75) Inventors: Jiang Gu, Guangdong (CN); Virginia M. Anderson, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 1087 days.

(21) Appl. No.: 13/384,094

(22) PCT Filed: Jul. 16, 2009

(86) PCT No.: PCT/US2009/050774
§ 371 (c)(1),
(2), (4) Date: Jul. 10, 2012

(87) PCT Pub. No.: WO2011/008209
PCT Pub. Date: Jan. 20, 2011

(65) Prior Publication Data
US 2012/0314049 A1    Dec. 13, 2012

(51) Int. Cl.
*H04N 7/18* (2006.01)
*G02B 21/36* (2006.01)
*G06F 19/00* (2011.01)

(52) U.S. Cl.
CPC ............ *G02B 21/365* (2013.01); *G06F 19/321* (2013.01)

(58) Field of Classification Search
None
See application file for complete search history.

(56) References Cited

U.S. PATENT DOCUMENTS

| 6,652,456 | B2  | 11/2003 | Gelfand et al. |
| 7,292,251 | B1  | 11/2007 | Gu et al. |
| 2004/0167806 | A1 | 8/2004 | Eichhorn et al. |
| 2006/0210142 | A1* | 9/2006 | Oguni et al. ............. 382/145 |
| 2008/0152207 | A1 | 6/2008 | Micheva et al. |

OTHER PUBLICATIONS

International Search Report of International App. No. PCT/US09/50774—Date of Completion of Search: Aug. 14, 2009.
Written Opinion of the International Searching Authority of International App. No. PCT/US09/50774—Date of mailing: Sep. 1, 2009.

\* cited by examiner

*Primary Examiner* — Sath V Perungavoor
*Assistant Examiner* — Janese Duley
(74) *Attorney, Agent, or Firm* — Locke Lord LLP (57) ABSTRACT

The virtual telemicroscope system (VTS) of the present invention captures an entire image of a specimen on a test slide as an original high power image, signal processes the original high power image to generate a low power background image, generates an initial virtual slide based on the low power background image and posts and/or transmits the initial virtual slide to a remote user enabling the remote user to view the low power background image on a remote user's computer screen. While viewing the initial virtual slide, the remote user may identify (i.e., select) one or more specific areas on the background image and request the service provider to provide detailed images (e.g., higher magnified image than the background image) at the defined locations. In response, the VTS provides the remote user with the requested partial high power image by simply signal processing the original high power image and generating a secondary virtual slide based on the newly processed image. This process can be repeated until the remote user is satisfied with the viewing.

18 Claims, 8 Drawing Sheets

VIRTUAL TELEMICROSCOPE

This application is a national phase entry under 35 U.S.C. §371 of International Application No. PCT/US2009/050774, filed Jul. 16, 2009, entitled "Virtual Telemicroscope", which is hereby incorporated by reference in its entirety.

BACKGROUND OF THE INVENTION

I. Field of the Invention

This invention relates generally to a virtual telemicroscope system (VTS) and, more particularly, to a method and system for using a computer system as a telemicroscope.

II. Background of the Related Art

Telepathology is a field that combines the disciplines of pathology, computer science and telecommunication. It captures, digitizes, transmits, displays and manipulates pathological and medical images for the purpose of analysis, consultation, collaboration, diagnosis; training and standardization. Compared with conventional pathology, telepathology is more efficient, economical and flexible. It enables medical image evaluation to be performed at any location, any time, as long as the evaluator has access to a computer with adequate network connection.

The history of telemedicine and telepathology goes back to the early days of computer science and telecommunication, and its progress has paralleled the advancement of these two fields. Physicians have long been experimenting with the idea of delivering medical service to distant locations by means of telecommunication.

Telemedicine has come a long way. Certain disciplines, such as teleradiology, have been successfully implemented in many hospitals throughout the world. However, telepathology and telemedicine face a number of obstacles. These include computer speed and capacity, programming techniques, compression strategy, network transmission bandwidth, the way the images are displayed and manipulated, physicians' and technicians' training, as well as administrative issues such as medical licensing, legality, payment, medical insurance, patient privacy, etc.

In addition, for telepathology in particular, much of the resistance to these new technologies from the pathology community has been that the microscopic images have been handled and viewed in a way that is very different from the traditional manner in which the cases are evaluated. The transmitted images are usually static, isolated, and often represent only portions of the entire tissue section. The pathologists frequently hesitate in making any pathologic diagnosis based on the computer images of a partial tissue section displayed in an unfamiliar manner. When the entire specimen is digitized, the process takes a considerable amount of time (a few hours), involving specially designed and expensive automatic microscopic equipment and lengthy scanning steps. This, together with the limited computer capacity, the relatively narrow transmission bandwidth and the very high cost, has hindered the practical value of this potentially very useful technology up to the present day.

With the recent development of fast computers, wide band transmission network and new programming technology, this situation is rapidly changing. This VT system takes advantage of recent advancements and overcomes some of the major technical obstacles in telepathology. It aims to popularize this technology with a new approach.

In an international conference on telepathology on Dec. 3-5, 1996, leading experts in the field of telepathology agreed that at sufficient resolution, the digitized computer images can be adequate for pathological diagnosis and consultation. There are systems for similar Purposes. However, no practical system was available to provide a pathologist with a full magnified or non-magnified view of the entire specimen and at the same time a desired view of selected portions of the specimen at a different magnification. The available systems rely on remotely controlled microscope and camera and broadband network connection, or lengthy process of digitization of slides, involving cost far beyond the justification of the practical value for most pathologists worldwide.

SUMMARY OF THE INVENTION

An object of the present invention is to provide a method and system of a virtual telemicroscope capable of communicating with a remote user via a network connection providing the remote user with a medical image such as a microscopic image of a human cell and tissue, and responding to a request from the remote user requesting a detailed image of a specific portion of the image interactively.

In an embodiment, the virtual telemicroscope system (VTS) of the present invention captures an entire image of a specimen on a test slide as an original image, signal processes the original image to generate a background image that represents an entire area of the original image but has a lower magnification value than the original image, generates an initial virtual slide based on the background image and transmits the initial virtual slide to the remote user enabling the remote user to view the background image on a remote user's computer screen. Alternatively, the initial virtual slide can be generated to include the low power background image as well as one or more higher power images of selected areas of interests, and a clear image map showing the relative geographic locations and sizes among these images can be packaged together as an initial virtual slide. While viewing the initial virtual slide, the remote user may identify (i.e., select) one or more specific areas of interests on the background image and request the service provider to provide detailed images (e.g., higher magnified image than the background image) at the defined locations. In response, the VTS provides the remote user with the requested high power images by simply signal processing the original image and generating another virtual slide based on the newly processed image. This process can be repeated until the remote viewer is satisfied with the viewing.

The further features, aspects will be better understood from the following detailed description and accompanying drawings.

DETAILED DESCRIPTION OF THE INVENTION

The above and other objectives of the invention will become more apparent from the following description and illustrative embodiments which are described in detail with reference to the accompanying drawings. Similar elements in each Figure may be designated by like reference numbers and, hence, subsequent detailed descriptions thereof may be omitted for brevity. Also, this application relates in part to Applicants' work described in U.S. Pat. No. 7,292,251 issued on Nov. 6, 2007 which is incorporated by reference herein in its entirety.

Figure 1:
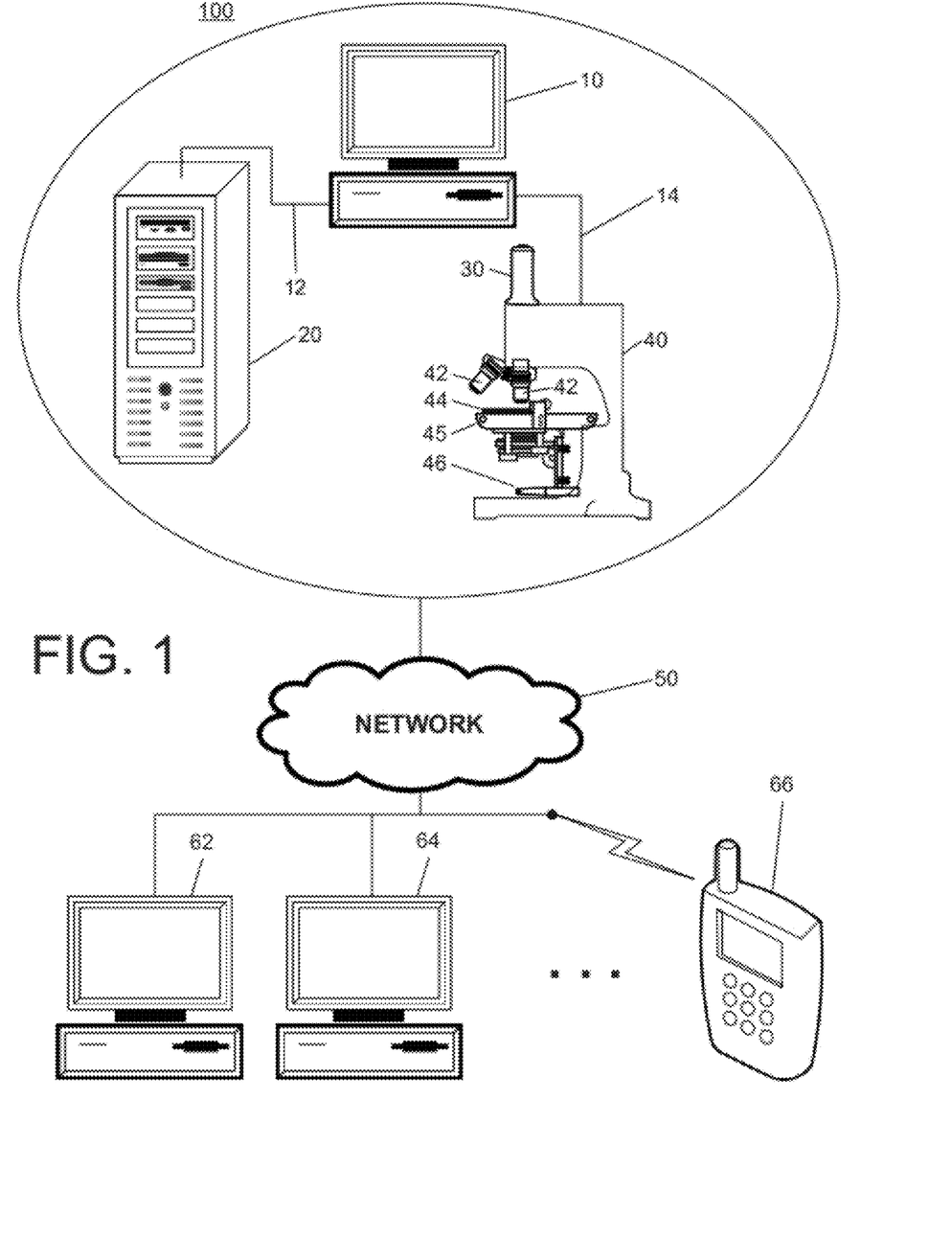
FIG. 1 illustrates a network connection by which the Virtual Telemicroscope System (VTS) 100 of the present invention is connected to remote users via a network.

FIG. 1 illustrates a Virtual Telemicroscope System ("VTS") 100 of the present invention connected to remote users 62, 64, 66 via a Network 50 (e.g., the Internet). The VTS comprises a computer system 10 connected to a server system 20 via a sub-network 12 (e.g., the LAN). The VTS is also connected, via another sub-network 14, to a digital image taking system 30 (e.g., a digital camera) which is again connected to a light microscope 40. In an embodiment, the computer system may include a processor with 2.53 GHz speed, 4 GB RAM and a built-in storage space (e.g., hard drive), and the server system may have at least 1000 GB storage space. While this embodiment uses a digital image taking system 30 such as a digital camera combined with a light microscope, a high resolution scanner may be used for the same purpose, i.e., instead of the digital camera combined with the light microscope. Also, most of the network connections used in the VTS either internally or externally can be established using wireless network connections. Also, a remote user may use a PC as well as other type of personal hand held devices such as a cellular phone or a media player (e.g., IPOD) equipped with an appropriate display screen to communicate with the VTS and view the images from the VTS.

Figure 2:
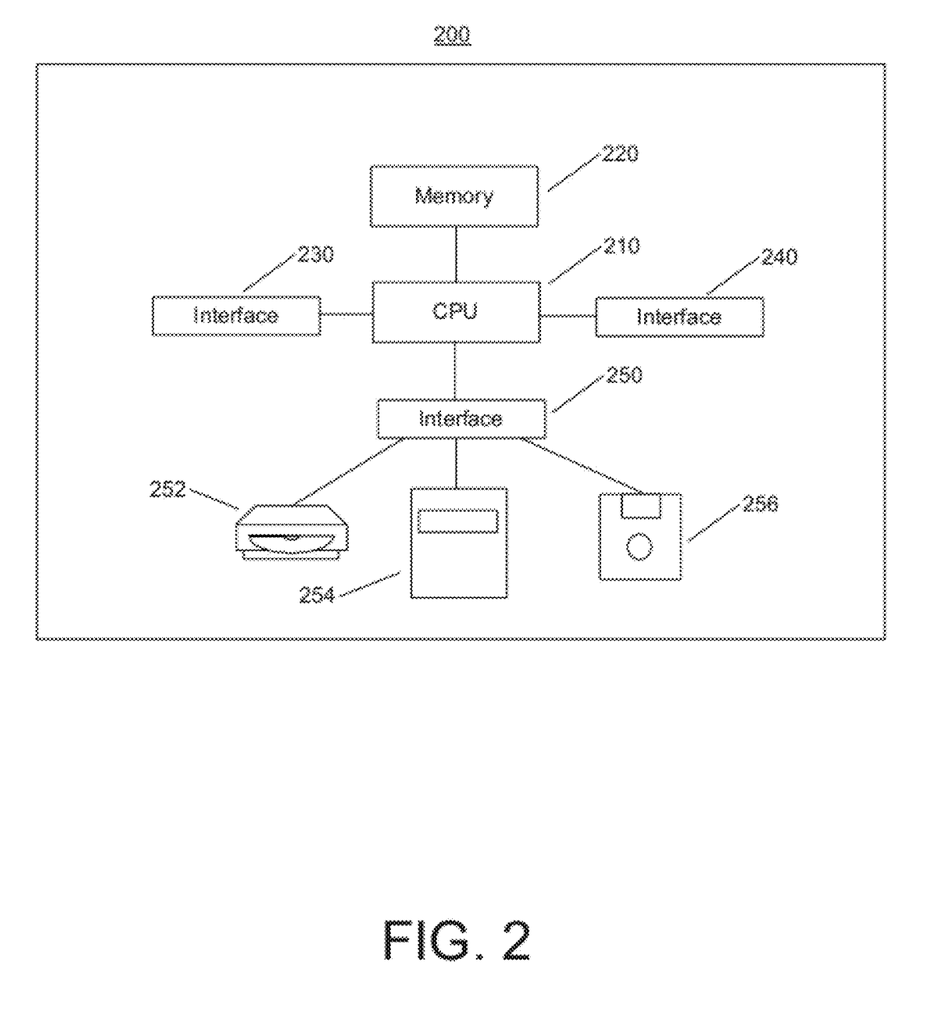
FIG. 2 is a block diagram of the computer system 10 within the VTS 100 as shown in FIG. 1.

FIG. 2 is a block diagram 200 of the computer system 10 as shown in FIG. 1 which includes a CPU 210 (e.g., with 2.53 GHz processing speed), Memory 220 (e.g., with 4 GB RAM) and an input interface 230 (e.g., for keyboard), an output interface 240 (e.g., for a monitor), a peripheral interface 250 (e.g., for storage devices such as CD 252, HD 254 and Floppy Disk 256).

In particular, the computer system 10 runs a proprietary VT program that performs, upon execution, major functions of the VTS such as capturing an original image from a physical slide coated with a specimen, signal processing the original image to generate, e.g., a low power background image and at lease one partial high power image, arranging the processed images with mapping information the defines the relative position of the partial high power image to the background image, generating a virtual slide based on the processed images along with the mapping information, and posting the virtual slide to the server system 20 so that the remote users can access the server for previewing and downloading the virtual slide for, e.g., a sample examination for a pathology. Each of the remote users may access the server system using the proprietary VT program running their own computer to view the virtual slide, and may place an order for an additional high power image to the service provider (i.e., the VTS) as a feedback process. Upon receiving the order (i.e., a request from a remote user), the VTS may signal process again for the requested image (e.g., a partial high power image) to generate and transmit another virtual slide with the requested partial high power image.

Figure 3:
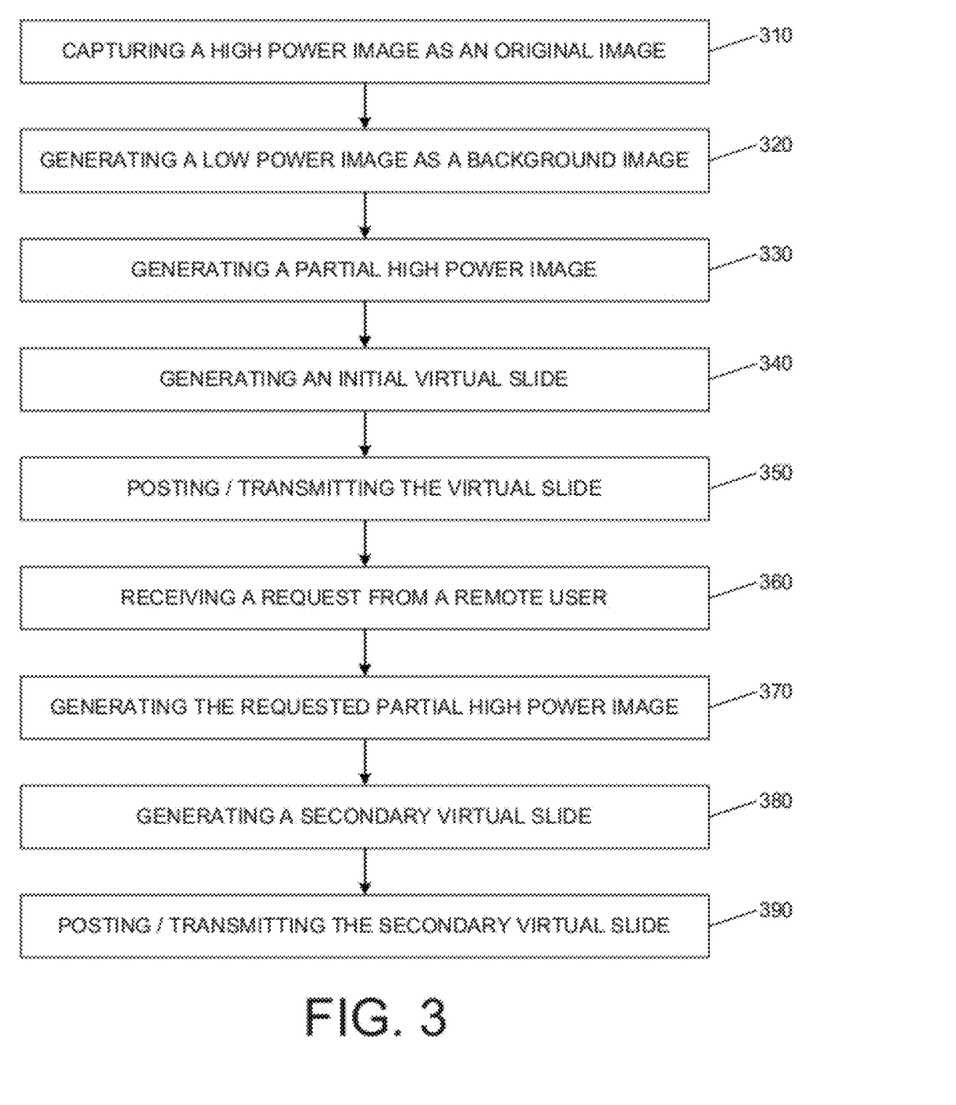
FIG. 3 is a flow chart illustrating the operation of an exemplary VTS 100 as shown in FIG. 1.

FIG. 3 is a flow chart illustrating the major operation of the VTS 100 as shown in FIG. 1. At step 310, an operator of the VTS may capture an image of a specimen (e.g., a test cell to be examined) located on a physical slide as an original high power image. For example, using the light microscope 40, the operator may place a glass slide 44 where a specimen of the test cell is laid on a slide support 45 and select one of the lenses 42 to take a picture of the entire slide using the associated digital camera 30. In this embodiment, the selected lens 42 of the light microscope 40 has a magnification of at least 100× for an original high power image.

Depending on the objective lens used on the light microscope, the entire image of the slide may be captured with one exposure as the original high power image. Alternatively, a series of exposures for multiple partial images may be taken consecutively, and then an entire image is formed by pasting the multiple partial images using the VT program for a seamless mosaic image that covers the entire slide image. Or, as described above, a high resolution scanner may scan the entire slide in strips and then piece them together as a seamless mosaic image.

It is recommended that the resulting high power original image has a resolution of at least 10,000×100,000 pixels depending on the size of the slide and area taken. The original high power image captured at step 310 may be stored in the HD 254 of the computer system using the VT program. It is to be understood that a plurality of original high power images (e.g., 20 images or more) each representing a plurality of different test slides may be captured and stored together in the computer system by the operator of the VTS.

At step 320, the VT program calls up the stored original high power image captured and stored at step 310, and signal processes the original high power image to generate a lower power image to be used as a background image of a virtual slide. The VT program may be configured in such a way that it reduces the magnification of the original high power image by reducing the resolution of the original high power image. That is, the VT program deletes a certain percentage of pixels from the original high power image to reduce the resolution and size of the image. For example, the VT program may delete one pixel for every four pixels on both the horizontal and virtual directions thereby maintaining an even distribution of the deleted and remaining pixels throughout the entire image area. The degree of the deletion may be calculated in advance according to predetermined target magnifications of the background image. In this embodiment, a background image having magnification of either 2×, 4×, 6×, 8×, 10×, 12×, 14×, 16×, 18× or 20× has been generated from the 100× original high power image. It is to be understood that if the background image is too large, the total size of the virtual slide would be too large as well making the transfer speed of the virtual slide slow.

Figure 4:
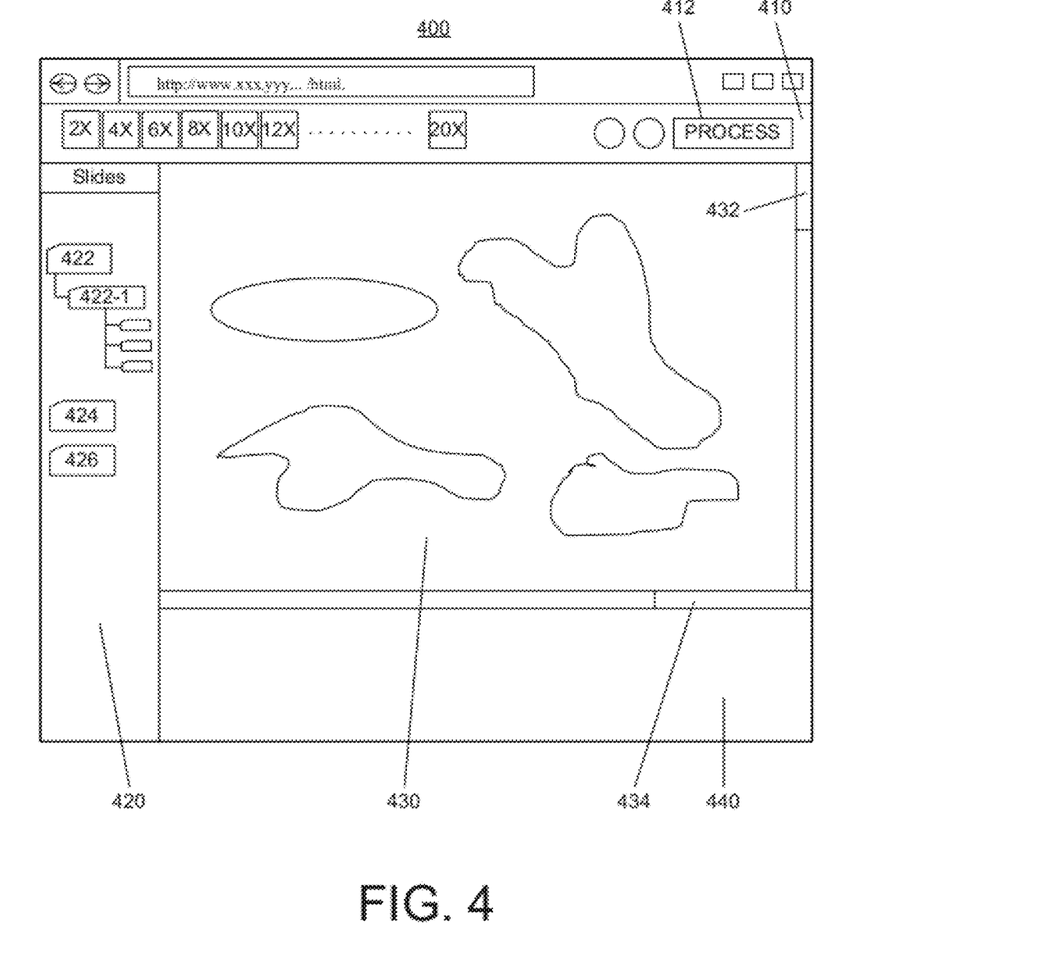
FIG. 4 shows an exemplary interface 400 of the VT program where an operator of the VTS 100 can generate a low power background image.

FIG. 4 shows an interface 400 of the VT program where the operator can view the captured original high power image and generate a lower power image having a predetermined magnification. The interface 400 includes an action pane 410 where the operator can select an action to be taken, a slide pane 420 where a list of available slides (i.e., original high power images) is shown, a display pane 430 where a selected original high power image is displayed, and an information pane 440 where the related information (e.g., the name and type of the test cell) of the displayed image is described. In an embodiment, the slide pane has a selectable tree type file structure in which the lower power image (e.g., 421-1) is connected to the associated original high power image (e.g., 422) as a sub-category. It is to be understood that the lower power image (e.g., 421-1) may have further sub-categories when more images are generated based on the low power image. In the current interface 400, the "further sub-categories" are indicated as blanks, meaning that there is no images generated under the low power image.

The operator of the VT program may select an original image by clicking on a file box (e.g. 422), and the selected original high power image will be displayed on the display pane 430. The operator may view and confirm the entire image by scrolling the image with the scroll bars 432, 434. The operator may then select the magnification of the to-be generated low power image (i.e., a background image) and click on the action button 412 (i.e., PROCESS) prompting the VT program to generate the low power image. Once the low power image is processed, it may be stored at the computer system 10 using the VT program which will associate the generated low power image with the original high power image to save with an appropriate file name and directory. Although the current interface 400 shows the original high power image, the interface will display the generated low power image when the operator clicks on the action button 412, i.e., as soon as the low power image is generated and available.

It is recommended that the converted low power image has a higher resolution than the remote user's computer screen on which the low power image will be displayed giving the remote user a power to view the displayed low power image with a magnifying function as well as a microscopic function. For example, if the converted low power image has 2000× 2000 pixels in size and displayed on a computer monitor having 800×600 pixels with 19-inch diagonal displaying area, it will represent a real enlargement of the original sample at about 100-150 times. On a computer monitor with a display capacity of 0.26-0.28 mm resolution, the real size of an image can be further stretched about 1.5 times without losing any visible resolution. As a result, a tissue section can be effectively enlarged up to about 200 times from the original size without any visible distortion of the original image. As a example, this would magnify a typical human neutrophil having a diameter of about 15 μm to about 3-4 mm in diameter giving an enough size to display microscopic patterns of cellular arrangement for most pathological cases. With this feature, the VT program may be configured to give the remote user an additional option to view the displayed image with a magnifying function, i.e., the displayed image whether it is low power image or a high power image can be magnified on the display pane.

At step 330, the operator of the VTS 100 may further generate one or more partial high power images of the original high power image. The partial high power images may be generated, for example, if the service provider already knows about the portions/areas of the original high power image that the remote users might be interested in viewing with more detailed images. The partial high power images may be generated based on the generated low power image using the VT program, i.e., the VT program may be adapted to generate the partial high power images by, for example, correlating the low power image to the original high power image. Alternatively, the partial high power images may be generated based on the original high power image as well. It is to be understood that these partial high power images will have magnification values somewhere between the high power image and the low power image. That is, the magnification of the partial high power image is higher than the low power image but equal to lower than the original high power image.

Figure 5:
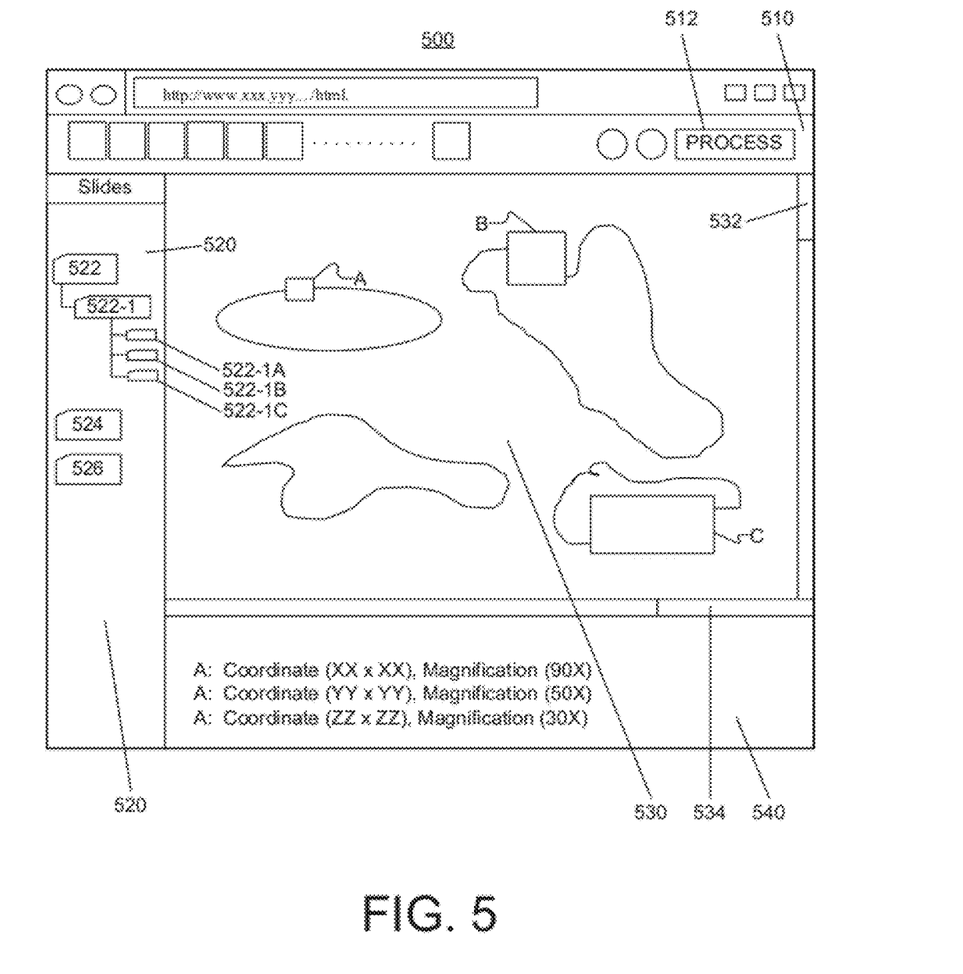
FIG. 5 shows an exemplary interface 500 of the VT program where the operator of the VTS 100 can generate one or more partial high power images.

FIG. 5 shows an exemplary interface 500 of the VT program where the operator of the VTS 100 can view the images (i.e., captured original high power image and generated low power image) and generate one or more partial high power images. The interface 500 may include multiple panes similar to the interface 400 including, for example, an action pane 510, a slide pane 520, a display pane 530 and information pane 540. The slide pane 520 shows clickable buttons 522, 524, 526 each represents an original high power image of different slides captured and stored in the computer system 10. Each of the clickable buttons may have sub-buttons (e.g., 522-1) that represents the low power image associated with the parent original high power image (e.g., 522). The sub-buttons may have another layer of sub-buttons (e.g., 522-1A, 522-1B, 522-1C) each represents the to-be generated partial high power images.

The display pane 530 of the interface 500 displays an image of a slide selected at the slide pane 520. The current view of the display pane shows the low power image 522-1 generated from the original high power image 522. The display pane 530 also has scroll bars 532 and 534 enabling the operator to scroll the images within the display pane.

While viewing the low power image on the display pane 530 of the interface 500, the operator may select (i.e., identify) a specific area on the low power image for generating a partial high power image. This can be done by several ways. For example, the operator using a mouse of the computer system 10 "points" a specific area and "drags" the mouse so that the specific area can actually be selected. In this embodiment, the VT program is configured in such a way that the size of the selected area by the operator corresponds to the intended magnification of the image of the selected area. For example, the higher the intended magnification of the selected area, the smaller the area it will cover on the background image. Alternatively, the VT program may utilize any other method to select the interested area on the background image such as selecting an area using the keyboard of the computer system.

Once the operator selects one or more areas A, B, C sequentially each with an appropriate size with relevant magnifications intending generating partial high power images, the VT program automatically indicates in the information pane 540 the relevant information of the selected areas sequentially such as the coordinates (i.e., geographical information of a selected area within the low power image) and magnifications of each of the selected areas A, B, C as shown in FIG. 5.

The operator then clicks on the action button "PROCESS" 512 allowing the VT program to process the selected areas A, B, C for partial high power images. The VT program may then save the processed images under the sub-directory of the corresponding low power image (e.g., 522-1) which will be displayed as 522-1A, 522-1B, 522-1C as an example. It is to be understood that the VT program may also save the geographical information of the partial high power images with respect to the low power image as mapping information as well we the magnification values. While the current view of the interface 500 displays the low power image on which the selected areas are overlapped, once the "PROCESS" button is clicked and the partial high power images are generated, these images (e.g., 522-1A, 522-1B, 522-1C) may be displayed on the display pane 530 as well.

Additionally, the VT program may also generate thumbnail images for each of the generated images (i.e., the low power image and the one or more high power partial images) and save them along with the generated images under the same directory. It is to be understood that all the partial high power images are processed in sizes equal to or larger than the resolution of the computer monitor (e.g., 800×600 pixels) and saved in an image file format such as JPG, GIF, TIF or BMP file formats. It is also to be understood that the highest magnification for the high power images would be the same magnification as the original high power image, i.e., 100× in this embodiment.

Figure 6:
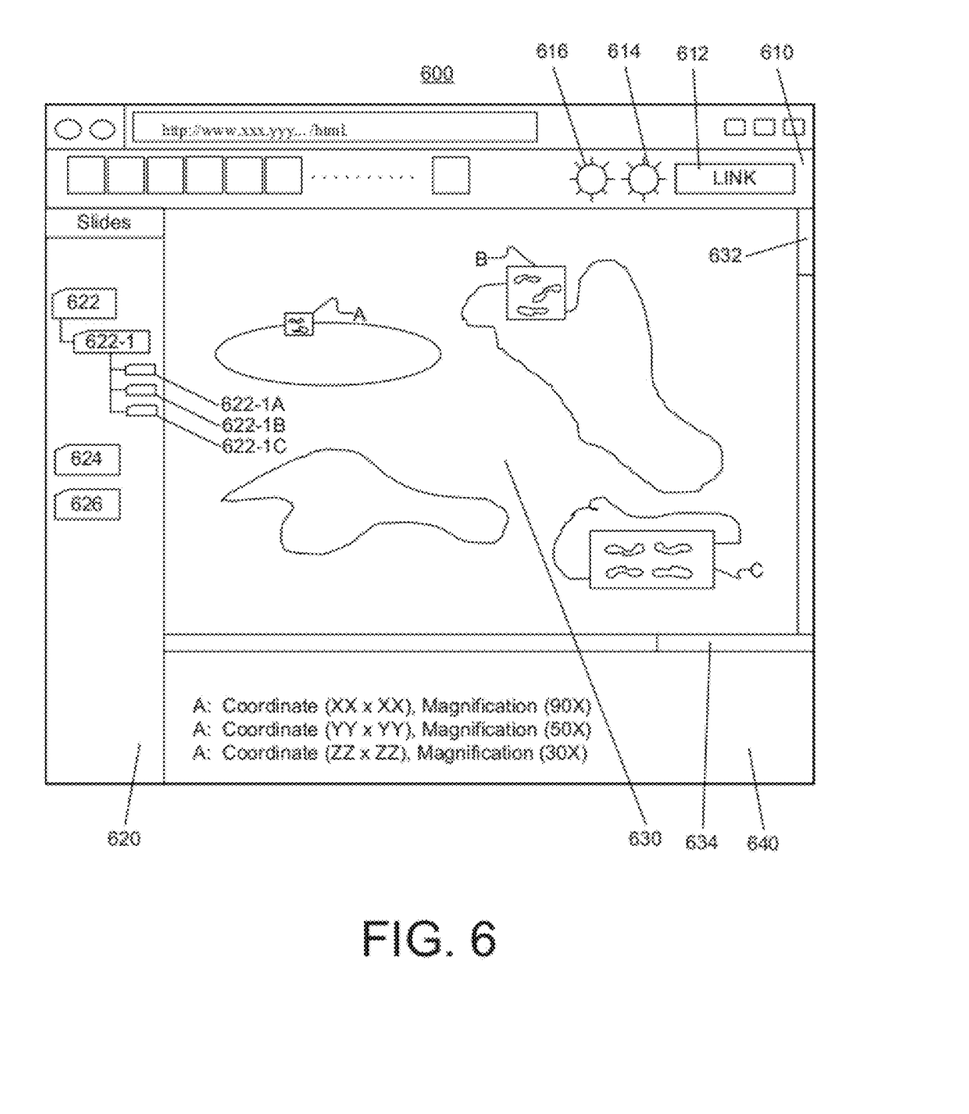
FIG. 6 shows an exemplary interface 600 of the VT program where the operator of the VTS 100 can generate a virtual slide while viewing the processed images.

At step 340, an initial virtual slide is generated based on the processed images and mapping information. FIG. 6 shows an exemplary interface 600 of the VT program where the operator of the VT system 100 can generate a virtual slide while viewing the processed images. Although the major appearance of the interface 600 is somewhat similar to the interface 500, the interface 600 actually displays not only the low power image as a background image but also the thumbnail images of the generated partial high power images on the relevant portions of the background image. For example, when the operator clicks on a button (e.g., 622-1) at the slide pane 620, the VT program displays the low power background image on the display pane 630 of the interface 600 along with the thumbnail images A, B, C at the relevant portions on the low power background image. That is, the positions of the thumbnail images are correlated with the areas from which they were processed and the sizes of the thumbnail images correspond to the magnifications of the partial high power image. It is to be understood that the display pane 630 also includes scroll bars 632, 634 to scroll the displayed image.

At this stage, the operator of the VTS 100 may add and/or delete partial high power images using the interface. For example, the operator may select an additional interested area using the mouse point in a similar manner where the operator selected an area at step 330, i.e., pointing and dragging the mouse point. The VT program may automatically creates a corresponding thumbnail image to display on the selected area on the low power image. Also, the interface 600 may be configured in such a way that the operator can select one of the thumbnail images A, B, C on the low power image displayed on the display pane 630, or identify one of the information text on the information pane 640 and request to delete the selected high power images. As an example, the operator may delete all of the thumbnail images thereby generating a virtual slide solely based on the low power image, i.e., without any partial high power images.

After confirming that all the partial high power images are correctly aligned as intended, the operator may click on the "LINK" button 612 prompting the VT program to generate a virtual slide for the selected slide (e.g., slide 622). The generated virtual slide may then be saved temporarily in the computer system 10 with a unique file name. As an example, the VT program may create an index file that compiles the file names for each image to save the virtual slide. The created index file may be saved with a unique extension such as "cct" or "cst" that will protect the file from being opened by a third party. The index file may also be saved with a popular format such as "txt".

At step 350, the VT program posts the virtual slide generated at step 340 to the server 20 connected to computer system via a sub-network 12 as illustrated in FIG. 1. The interface 600 may be configured in such a way that after confirming the generation of the virtual slide at step 340 (i.e., after clicking on the "LINK" button 612), an action button (e.g., 614) is highlighted to initiate the posting of the generated virtual slide to the server 20. Alternatively, the operator may initiate an email program by clicking another highlighted action button (e.g., 616) to directly send the generated virtual slide to the remote user with an attached email message.

The remote user 62 can now access to the server 20 for the posted virtual slide using a computer (e.g., PC) that runs the VT program. For example, the remote user opens the VT program and type in the web address of the server 20. An appropriate billing system along with a login system may be adapted to the VT program to allow an access to the server. Upon obtaining the access to the server, the remote user may navigate the file folders of the server (e.g., the slide pane) to locate the virtual slide of interest. Alternatively, as described above, the remote user may open an email attached with the virtual slide from the VTS and view the image of the virtual slide using the VT program.

Figure 7:
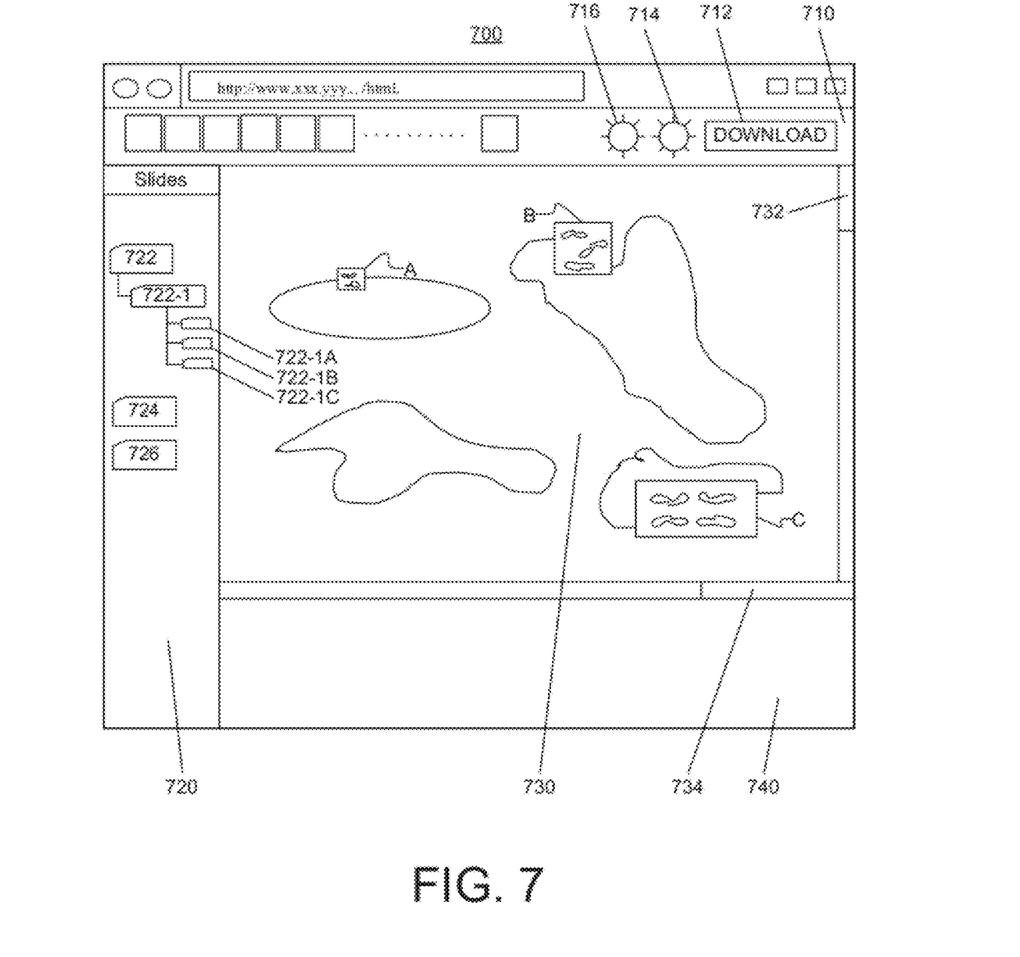
FIG. 7 shows an interface 700 of the VT program where the remote user can preview the virtual slide after obtaining an access to the server.

FIG. 7 shows an interface 700 of the VT program where the remote user can preview the virtual slide after obtaining an access to the server, or after opening the email from the VTS. The interface 700 includes an action pane 710, a slide pane 720 that lists a file folder directory of the virtual slides saved in the server 20, a display pane 730 that displays thumbnail images of a selected virtual slide as a preview image, and information pane 740 that describes a detailed information of the selected virtual slide such as the name and characteristics of the virtual slide, taken time and place of the images, and the name of the lab that the images have been taken etc. As an example, the remote user may initially navigate the file folder directory of the slide pane 720 and locate a slide (e.g., slide 722). When the remote user clicks on a highlighted action button (e.g., a preview button 714), the VT program displays the preview image of the selected slide on the display pane 730 which include the background image and partial high power images. The display pane 730 also includes scroll bars 732, 734 to scroll the displayed image.

Figure 8:
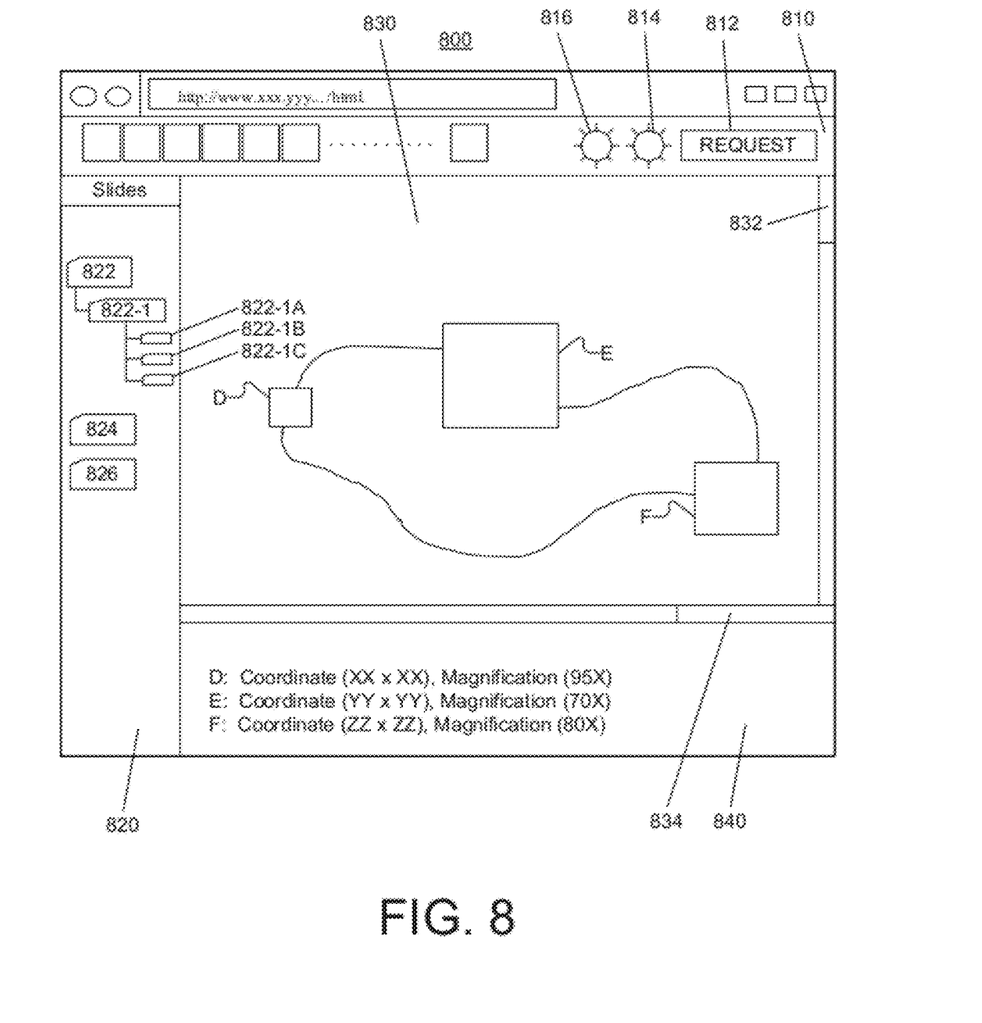
FIG. 8 shows an interface 800 of the VT program where the remote user views the downloaded images of the selected virtual slide.

While viewing the preview image of the selected virtual slide (e.g., slide 722) on the display pane 730, the remote user may click on the "DOWNLOAD" button 712 on the action pane 710 prompting the VT program to download the selected virtual slide from the server 20 to the remote user's computer 62. The VT program may provide the remote user with a new interface 800 as shown in FIG. 8. It is to be understood that the remote user does not need to download the image from the server if he or she received the virtual slide with an email attachment from the VTS.

FIG. 8 shows an interface 800 of the VT program where the remote user views the downloaded images of the selected virtual slide. The interface 800 may have similar set up to the other interfaces as described above but the slide pane 820 of the interface 800 lists the images of the virtual slides that are already downloaded to the remote user's computer. For example, the slide pane 820 of the interface lists the downloaded virtual slide 822 that includes three high power images 822-1A, 822-1B, 822-1C associated with the lower power background image 822-1 already downloaded to the remote user's computer. When the remote user clicks on one of the images (e.g., 822-1, 822-1A, 822-1B, 822-1C), the selected image is displayed on the display pane 830 of the interface. The current view of the display pane shows that the remote user selected the high power image 822-1A of virtual slide 822, as an example. It is to be understood that the remote user may also select the low power background image 822-1 for a display on the display pane. The display pane includes scroll bars 832 and 834 for the remote user to move around the displayed image on the display pane.

Although, the above description regarding the manipulation of the downloaded images by the remote user is based mainly on an assumption that the virtual slide is posted on the server 20 by the operator of the VTS, it is to be understood that the remote user may can perform similar actions to manipulate the images when the virtual slide is sent by an email attachment. That is, once the VT program detach the virtual slide from the email, it can be regarded as downloaded files and the remote user can view the images in the virtual slide by performing similar activities using the similar interfaces as described above.

While the remote user views the downloaded images displayed on the display pane 830, the remote user may request additional high power images to the VT system using the interface 800, i.e., in addition to the partial high power images already provided thereby initiating a feedback process. For example, the remote user may point and drag the mouse pointer to select additional interested areas (e.g., E, D, F) on the displayed image (e.g., 822-1A) as shown in FIG. 8. The information pane 840 may automatically display a real-time information for the selected area such as the coordinate and magnification of the areas selected by the remote user. The VT program of the remote user is configured in a similar manner to the VT program of the operator that the size of the selected area is correlated with the magnification of the selected area, i.e., the higher the intended magnification, the smaller the area it will cover on the background image. In this example, the high power image 822-1A is used and acting as a background image for the remote user to select the additional areas (e.g., E, D, F) for requesting further magnified images. It is to be understood that the user may go back to select the low power background image (i.e., 822-1) in the slide pane 820 to request more areas of partial high power images. Upon selecting the areas (e.g., D, E, F), the remote user clicks on the "REQUEST" button 812 on the action pane 810 and the VT program of the remote user side will convey the request to the VTS 100.

The remote user may communicate with the computer system 10 of the VTS 100 with a number of means, mostly built in the VT program. As an example, an email function may be activated within the VT program interface 800 utilizing the email program of the remote user's computer. Alternatively, other communication means such as video conferencing, whiteboard image sharing, chat room, and Internet phone may be used as well. Also, the VT program (e.g., interface 800) may adapt some of commercially available software with extra buttons (e.g., buttons 814, 816) within the VT program making the VT program a more complete system for conducting the telepathology.

At step 360, the VT program receives the request from the remote user via the Internet 50. The request may include one or more specific areas (e.g., D, E, F) on the entire area of the low power background image and magnification of the requested partial high power images. Alternatively, the VT program may receive the request with various communication means.

At step 370, upon receiving the request at step 360, the VT program retrieves the original high power image taken and stored at step 310 from the computer system 10, and processes it to generate the requested partial high power images. Since the original high power image is already captured and stored in the computer system 10, there is no need to capture an additional image at this stage, i.e., the VT program may simply process the stored original high power image to generate the requested partial high power images according to the requested information.

At step 380, the VT program generates another virtual slide (i.e., a secondary virtual slide) based on the newly generated partial high power images and the already stored low power background image along with the mapping information between these images. The generating method of the secondary virtual slide may be similar to the generating method of the initial virtual slide as in step 340.

At step 390, the VT program may post the generated secondary virtual slide to the server 20 and prompts the remote user to download the secondary virtual slide. Alternatively, the VT program may send an email attached with the secondary virtual slide to directly send it to the requesting party, i.e., remote user. The remote user may view the images in the secondary virtual slide and may repeat the request multiple times until the remote user is satisfied with the examination/evaluation of the virtual slide.

As described above, once the original high power image is captured and stored in a computer system of the VTS 100, the rest of the processes, including generating the virtual slide, posting/transmitting the virtual slide, receiving the request from the remote user, processing additional partial high power images, generating the secondary virtual slide and secondary posting/transmitting of the secondary virtual slide to the requesting remote user, can be designed with an automatic process, i.e., with no human individual involved. Moreover, the service provider of the VTS does not need to take, package and send multiple high power partial images from interested areas in advance for the feedback service, i.e., no additional capturing of new images with hardware is necessary for the service provider of the VTS in the feedback process. As a result, the transaction of the request from the remote users may be expedited with less errors. Moreover, if an automatic slide tray is used in an appropriate way to automatically capture the original high power image, the VTS may become a fully automated system.

The present invention utilizes and takes benefits an improved computer processing capacity and speed, camera resolution, network speed (e.g., a high speed Internet), and information compression and storage technology. The present invention may be embodied as systems, methods, and/or computer program products. Accordingly, the present invention may be embodied in hardware and/or in software (including firmware, resident software, micro-code, etc.). Furthermore, the present invention may take the form of a computer program product on a computer-readable storage medium having computer-readable program code embodied in the medium for use by or in connection with an instruction execution system. In the context of this document, a computer-readable storage medium may be any medium that can store, the program for use by the instruction execution system, apparatus, or device.

The computer-readable medium may be, for example but not limited to, an electronic, magnetic, optical, electromagnetic, or semiconductor system, apparatus, device, or medium. More specific examples (a nonexhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

It will be appreciated by persons skilled in the art that the present invention is not limited to what has been particularly shown and described in this specification. Rather, the scope of the present invention is defined by the claims which follow. It should further be understood that the above description is only representative of illustrative examples of embodiments. For the reader's convenience, the above description has focused on a representative sample of possible embodiments, a sample that teaches the principles of the present invention. Other embodiments may result from a different combination of portions of different embodiments.

The description has not attempted to exhaustively enumerate all possible variations. The alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent.

What is claimed is:

1. A method of using a computer system as a virtual telemicroscope that enables an interactive communication between a remote user and a service provider of the virtual telemicroscope, comprising:
   capturing a first image as an original high power magnification image corresponding to an entire area of a specimen on a slide with a digital image capturing device;
   signal processing of the first image to generate a second image as a background image that represents an entire area of the first image, but has a lower magnification than the first image;
   generating a virtual slide based on the second image and making the virtual slide available to the remote user;
   signal processing of the first image to generate a third high power magnification image that represents an area less than the entire area of the first image, in response to a request from the remote user; and
   delivering the third image to the remote user.

2. The method according to claim 1 further comprising storing the original first image into the computer system.

3. The method according to claim 1, wherein the step of signal processing of the first image to generate the second image also generates a fourth image as a partial high power magnification image corresponding to an area less than the entire area of the first image, the fourth image has an equal to or a lower magnification than the first image, but has a higher magnification than the second image, and the virtual slide generating step generates the virtual slide based on the second image and the fourth image.

4. The method according to claim 3 further comprising generating a linking information map indicating a regional relationship between the second image and the fourth image, wherein the step of generating the virtual slide generates the virtual slide by using the linking information map.

5. The method according to claim 1, wherein the service provider of the virtual telemicroscope sends an email attached with a generated virtual slide to the remote user.

6. The method according to claim 1 further comprising repeating the steps of the signal processing of the first image to generate the third image and delivering the third image to the remote user.

7. The method according to claim 1, wherein the magnification of the first image taken at the capturing step ranges at least 100× or higher.

8. The method according to claim 1, further comprising generating a thumbnail image for the second image and including the thumbnail image to the virtual slide.

9. The method according to claim 1, wherein the remote user is connected to the virtual telemicroscope with a wireless connection.

10. A virtual telemicroscope system that enables an interactive communication between a remote user and a service provider of the virtual telemicroscope, comprising:
    a digital image capturing device configured to capture a first image as an original high power magnification image corresponding to an entire area of a specimen on a slide;
    a computer system configured to signal process the first image to generate a second image as a background image that represents an entire area of the first image, but has a lower magnification than the first image;
    the computer system further configured to generate a first virtual slide based on the second image and make the virtual slide available to the remote user;
    the computer system further configured to signal process the first image to generate a third high power magnification image that represents an area less than the entire area of the first image, in response to a request from the remote user;
    a server configured to deliver the third image to the remote user.

11. The virtual telemicroscope system according to claim 10, wherein the computer system configured to signal process the first image to generate the second image also generates a fourth image as a partial high power magnification image corresponding to an area less than the entire area of the first image selected by the service provider of the virtual telemicroscope, the fourth image has an equal to or a lower magnification than the first image, but has a higher magnification than the second image, and the computer system further configured to generate the virtual slide generates the virtual slide based on the second image and the fourth image.

12. The virtual telemicroscope system according to claim 11 further comprising the computer system further configured to generate a linking information map indicating a regional relationship between the second image and the fourth image, wherein the computer system generating the first virtual slide generates the virtual slide by using the linking information map.

13. The virtual telemicroscope system according to claim 10, further comprising the computer system further configured to send an email attached with a generated virtual slide to the remote user.

14. The virtual telemicroscope system according to claim 10, wherein the magnification of the first image taken by the mean for capturing ranges at least 100× or higher.

15. The virtual telemicroscope system according to claim 10, further comprising the computer system further configured to generate a thumbnail image for the second image and the computer system further configured to include the thumbnail image to the virtual slide.

16. A system for using a computer system as a virtual telemicroscope that enables an interactive communication between a remote user and a service provider of the virtual telemicroscope, comprising:
    a memory unit;
    a processing unit in communication with the memory unit, wherein the processing unit is configured to:
    capture a first image as an original high power magnification image corresponding to an entire area of a specimen on a slide with a digital image capturing device;
    process the first image to generate a second image as a background image that represents an entire area of the first image, but has a lower magnification than the first image;
    generate a virtual slide based on the second image and make the virtual slide available to the remote user;
    process the first image to generate a third high power magnification image that represents an area less than the entire area of the first image, in response to a request from the remote user;
    deliver the third image to the remote user.

17. A computer-readable nontransitory medium that stores instruction codes for a method of using a computer system as a virtual telemicroscope that enables an interactive communication between a remote user and a service provider of the virtual telemicroscope comprising instruction codes for:

capturing a first image as an original high power magnification image corresponding to an entire area of a specimen on a slide with a digital image capturing device;

signal processing of the first image to generate a second image as a background image that represents an entire area of the first image, but has a lower magnification than the first image;

generating a virtual slide based on the second image and making the virtual slide available to the remote user;

signal processing of the first image to generate a third high power magnification image that represents an area less than the entire area of the first image, in response to a request from the remote user;

delivering the third image to the remote user.

18. A method of using a computer system as a virtual telemicroscope that enables an interactive communication between a remote user and a service provider of the virtual telemicroscope, comprising:

capturing a first image as an original high power magnification image corresponding to an entire area of a specimen on a slide with a digital image capturing device;

signal processing of the first image to generate a second image as a background image that represents an entire area of the first image, but has a lower magnification than the first image;

generating a first virtual slide based on the second image;

posting the first virtual slide to a server associated with the computer system allowing the remote user to access the server for the virtual slide;

receiving a request from the remote user requesting a third high power magnification image that represents an area less than the entire area of the first image and has a magnification equal to or lower than the first image, but higher than the second image;

signal processing of the first image to generate the third high power magnification image requested by the remote user;

generating a second virtual slide based on the second image and the third image along with mapping information that represents relative position of the third image with respect to the second image; and     posting the second virtual slide to the server, thereby allowing the remote user to access the server and view the second virtual slide.

* * * * *